United States Patent
Fishkin et al.

(10) Patent No.: US 7,274,028 B2
(45) Date of Patent: Sep. 25, 2007

(54) CHARACTERIZING FLUORESCENT AND/OR PHOSPHORESCENT MATERIALS

(75) Inventors: Joshua B. Fishkin, Long Beach, CA (US); Isaac Richman, Newport Coast, CA (US)

(73) Assignee: The Boeing Company, Chicago, IL (US)

( * ) Notice: Subject to any disclaimer, the term of this patent is extended or adjusted under 35 U.S.C. 154(b) by 165 days.

(21) Appl. No.: 11/182,050

(22) Filed: Jul. 14, 2005

(65) Prior Publication Data

US 2007/0012884 A1    Jan. 18, 2007

(51) Int. Cl.
*G01J 1/58* (2006.01)
*G01B 9/02* (2006.01)

(52) U.S. Cl. .............................. 250/459.1; 250/458.1; 250/551; 356/484

(58) Field of Classification Search .................... None
See application file for complete search history.

(56) References Cited

U.S. PATENT DOCUMENTS

| | | | |
|---|---|---|---|
| 4,840,485 A | 6/1989 | Gratton | |
| 5,212,386 A | 5/1993 | Gratton et al. | |
| 5,257,202 A | 10/1993 | Gratton et al. | |
| 5,293,213 A * | 3/1994 | Klein et al. | 356/484 |
| 5,323,010 A | 6/1994 | Gratton et al. | |
| 5,416,582 A * | 5/1995 | Knutson et al. | 356/484 |
| 5,485,530 A | 1/1996 | Lakowicz et al. | |

OTHER PUBLICATIONS

Gratton, E. et al, A Continuously Variable Frequency Cross-Correlation Phase Fluorometer with Picosecond Resolution, Biophys. J. 44, 315-324 (1983).
Feddersen, B. et al, Digital Parallel Acquisition in Frequency Domain Fluorometry, Rev. Sci. Inst. 60(9), 2929-2936 (1989).
Piston, D. et al, Wide-Band Acousto-Optic Light Modulator For Frequency Domain Fluorometry and Phosphorimetry, Rev. Sci. Inst. 60(8), 2596-2600 (1989).
Feddersen B Digital Frequency Domain Fluorometry and the Study of Hoechst 33258 Dye-DNA Interactions. PhD. Thesis, Dept. of Physics, University of Illinois at Urbana-Champaign (1993).
Fishkin, J. et al, Gigahertz Photon Density Waves in a Turbid Medium: Theory and Experiments, Phys. Rev. E. 53, 2307-2319 (1996).

* cited by examiner

*Primary Examiner*—David Porta
*Assistant Examiner*—Frederick F Rosenberger
(74) *Attorney, Agent, or Firm*—Harness, Dickey & Pierce, P.L.C.

(57) ABSTRACT

A method spectrally and temporally characterizing the fluorescence and/or phosphorescence of a material includes using a frequency-domain cross-correlation fluorometer-phosphorimeter employing an interferometer. A flux-modulated excitation signal is used to excite the material. An interferometer is used to generate an optical path difference (OPD) between portions of an emission signal produced by the excited material to obtain an optical interference signal. The optical interference signal is detected by a heterodyning detection system to determine phase shift and demodulation of the emission signal relative to the excitation signal. Phase shift and demodulation data are acquired at a series of OPD values generated by the interferometer and at a plurality of light source flux-modulation frequencies at each OPD to spectrally and temporally resolve the emission signal.

20 Claims, 3 Drawing Sheets

CHARACTERIZING FLUORESCENT AND/OR PHOSPHORESCENT MATERIALS

FIELD OF THE INVENTION

This application is related to analysis of materials and more particularly (but not exclusively) to characterization of fluorescent and/or phosphorescent materials.

BACKGROUND OF THE INVENTION

Trace material analysis has many applications in biochemistry, medicine, homeland security, environmental science and other related fields. Accordingly, there is great interest in finding ways to rapidly characterize trace materials and to assess their molecular dynamics. Trace materials containing fluorescent and/or phosphorescent molecules may be identified uniquely or within a class by measuring their steady-state emission spectra.

Fluorescence flux at a specific emission wavelength may be measured by using an intensity-modulated laser light source in combination with a time-resolved single-detector system and a monochromator. The monochromator-based single-detector system, however, does not provide high optical throughput. Low throughput results in lowered signal-to-noise ratio and increased data acquisition times. Long acquisition times are undesirable, particularly where unstable or fragile molecular systems are concerned.

Fluorescence may also be measured using a dispersive instrument incorporating a detector array. Multiple emission wavelengths may be acquired in parallel, with temporal resolution possible in each spectral bin given adequate detector-array response time. The dispersive/detector-array system may allow for more rapid data acquisition than the monochromator-based system, but can suffer from inadequate detector array response time. Thus it can be difficult to characterize the temporal response of each spectral bin to assess the molecular dynamics of some fluorescent systems. The dispersive/detector-array system also can suffer from poor optical throughput, thus further limiting its efficacy relative to weakly emitting trace materials. Calibrating the dispersive detector-array system typically is complex. Each detector element is a distinct sensor which must be calibrated to minimize critical detector-to-detector response error.

SUMMARY OF THE INVENTION

The present invention, in one implementation, is directed to a method of characterizing fluorescence and/or phosphorescence of a material. An excitation signal is used to excite the material. An optical path difference is introduced between portions of an emission signal produced by the excited material to obtain an interference signal. The interference signal and a cross-correlation frequency of the interference and excitation signals are used to resolve the emission signal.

In one configuration of the invention, an apparatus for characterizing fluorescent and/or phosphorescent material includes an excitation source that provides an excitation signal for exciting the material. An interferometer is configured to receive an emission signal from the excited material and provide an optical path difference between portions of the received emission signal to produce an interference signal at a single detector. A heterodyning detection system is configured to mix a cross-correlation signal of the excitation signal with the detected interference signal to resolve the emission signal.

In another configuration, an apparatus for spectrally and temporally characterizing fluorescent and/or phosphorescent material includes means for producing a flux modulation frequency to excite the material, and means for splitting an emission signal from the excited material. The apparatus includes means for providing an optical path difference between portions of the split signal to produce a signal representative of interference between the portions, and means for detecting the signal representative of interference. The apparatus also includes means for mixing a cross-correlation frequency of the flux modulation frequency with the detected signal to obtain a mixed signal, and means for using the mixed signal to resolve the emission signal.

The features, functions, and advantages can be achieved independently in various embodiments of the present inventions or may be combined in yet other embodiments.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiments is merely exemplary in nature and is in no way intended to limit the invention, its application, or uses. For purposes of clarity, the same reference numbers may be used in the drawings to identify similar elements. Configurations of the present invention may be used in connection with fluorescent materials and/or phosphorescent materials. For purposes of convenience and brevity, unless otherwise indicated, "fluorescence" and "fluorescent" are used in this description to refer to fluorescent and/or phosphorescent materials.

In order to adequately characterize fluorescent materials and assess system molecular dynamics, it is highly desirable to rapidly perform broad-band, high-spectral resolution, time-resolved fluorescence intensity measurements, with the time resolution on a picosecond- to nanosecond-scale. Low signal-to-noise ratios and long data-acquisition times could hamper ability to adequately characterize weakly emitting, fragile and/or unstable molecular systems via the above mentioned combination of spectrally-resolved and time-resolved measurements. A high optical throughput instrument, with the above mentioned spectral and temporal measurement capabilities, is therefore desirable, particularly where trace materials are concerned.

Accordingly, in various configurations of the present invention, time resolved fluorescence and/or phosphorescence emission spectra are generated and measured, at impulse-response scales ranging from sub-picoseconds to milliseconds at wavelengths spanning, for example, the near-UV, visible and infrared portions of the electromagnetic spectrum. In one configuration, a flux-modulated light source is used to excite fluorescent and/or phosphorescent molecules in a given sample into an electronically excited state. The light source may be sinusoidally flux modulated or pulsed at a fixed frequency. The molecules fluoresce and/or phosphoresce (i.e., emit photons) over one or more spectral bands, with one or more characteristic decay times. An interferometer is used to spectrally resolve the fluorescence and/or phosphorescence. The flux-modulated light source and a phase and amplitude detection system are used to temporally resolve the fluorescence and/or phosphorescence intensity response.

An example of how one configuration of the present invention may operate shall now be described with reference to FIG. 1. In the present example, a sinusoidally flux-modulated laser or other source of visible or near-ultraviolet (near-UV) light illuminates and excites a fluorescent material having absorption regions in the visible and/or near-UV and an emission spectrum within the near-UV to visible to near-infrared portion of the electromagnetic spectrum. A graph showing intensity relative to time is indicated generally in FIG. 1 by reference number 20. The graph 20 illustrates evolution over time of intensity from the sinusoidally intensity-modulated excitation light source (represented by a curve 24) and a resultant emission from the fluorescent sample (represented by a curve 28). When the flux-modulated excitation 24 is purely sinusoidal, the emitted fluorescence radiance 28 varies sinusoidally versus time, with the same modulation frequency as the flux-modulated light source, but shifted in phase and partially demodulated because of fluorescence lifetime(s) and quantum yield of emitting flurophore(s). As further described below, phase lag $\phi$, excitation amplitude $AC_{ex}$, fluorescence amplitude $AC_{fl}$, average excitation intensity $DC_{ex}$ and average fluorescence intensity $DC_{fl}$, are parameters which are measured in the frequency domain in accordance with various configurations of the present invention. It should be noted generally that "measurement", "measuring" or the like as used in this description and/or the claims includes direct measurement, indirect measurement and/or other additional or alternative determination(s).

Figure 2:
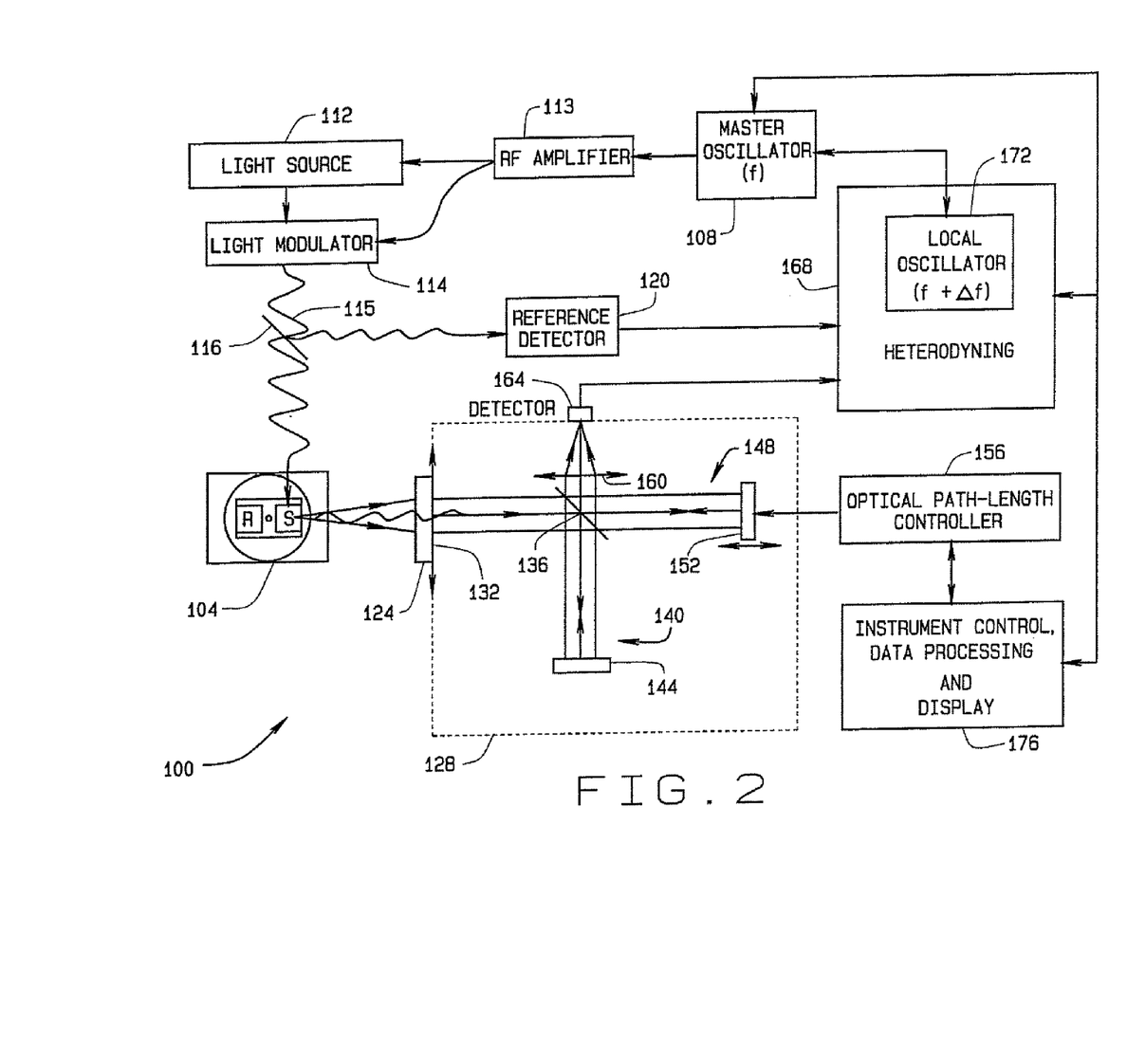
FIG. 2 is a schematic diagram of an apparatus for characterizing a fluorescent and/or phosphorescent material in accordance with one configuration of the present invention.

One exemplary configuration of an apparatus for characterizing a fluorescent and/or fluorescent material is indicated generally in FIG. 2 by reference number 100. The apparatus 100 includes a rotating sample holder 104, which can rotate 180 degrees so that a sample material and a reference material can be alternately illuminated. The sample holder may hold an unknown sample S (i.e., unknown emission spectrum and unknown fluorescence lifetime), and a reference material R having a known fluorescence lifetime and a known emission spectrum, to be sequentially illuminated as further described below. A reference material may be measured to calibrate the apparatus 100, e.g., to compensate for detector- and/or electronics-induced electronic phase shifts and/or modulation. In another configuration, a non-rotating sample holder could be used.

A master oscillator 108 produces a signal that is used to flux-modulate light from a light source 112. In the present exemplary configuration the oscillator signal is a radio-frequency (RF) signal, amplified by RF amplifier 113, although other configurations are contemplated in which a non-radio-frequency signal is used. The light source 112 may include, for example, a continuous wave (CW) laser or other incoherent steady-state source of visible or near ultraviolet (UV) light. The light from the source 112 passes through light modulator 114 (e.g., a wide-band acousto-optic light modulator) to provide a beam of light 115 that is flux-modulated at a first frequency f. In another configuration, the light may be pulsed at a fixed fundamental first frequency and contain harmonic content thereof (e.g., a mode-locked laser could be used as a light source). The flux-modulated light is split by a beam splitter 116 and strikes a reference detector 120 and the material in the sample holder 104. Sinusoidally flux-modulated fluorescence passes through an optional filter 124 to an interferometer 128. The filter 124 may be a long-wavelength-pass filter for excluding exciting radiation from the interferometer 128. The interferometer 128 is a Michelson interferometer, although other types of interferometric systems, including but not limited to a variety of amplitude splitting interferometers or wavefront-splitting interferometers, could be used.

The interferometer 128 includes a collimator 132, a beam splitter 136, a first arm 140 having a stationary mirror 144, and a second arm 148 having a movable mirror 152. The movable mirror 152 is controlled via an optical path-length controller 156. The interferometer 128 can generate optical interference over a desired range of optical path differences between the arms 140 and 148. The interferometer 128 also includes a condenser 160 that focuses the fluorescence and/or phosphorescence from the material sample onto a detector 164. The detector 164 may include, for example, a photodiode detector, although other or additional types of detectors, such as photomultiplier tubes, an avalanche photodiode system, a charge coupled device detector, or microchannel plate detectors also are contemplated. Configurations of the present invention also are contemplated in which an array of detectors is used instead of the single detector 164.

Signals from the master oscillator 108, reference detector 120 and detector 164 are sent to a heterodyning detection system 168, which includes a local oscillator 172 that produces an amplitude modulated signal at a second frequency of $f+\Delta f$. The master oscillator 108 and the local oscillator 172 each include a phase-locked loop frequency synthesizer. The oscillators operate coherently with each other off of a single quartz crystal in the master oscillator 108, with the local oscillator 172 acting in slave relationship to the master oscillator 108. Instrument control, data processing and display elements 176 are in communication with the master oscillator 108, the optical path length controller 156, and the heterodyning detection system 168 (and with the rotating sample holder 104, if desired).

The detector 164 is configured to provide phase and amplitude detection. Phase is determined by comparing the signal detected by the reference detector 120 with the signal detected by the detector 164. For a given optical path difference (OPD) between the interferometer arms 140 and 148, phase, amplitude and average flux density of the fluorescence are measured at a plurality of flux-modulation frequencies of the light source 112. The measurements of phase, amplitude and average flux density at a plurality of laser-source flux-modulation frequencies are repeated over an appropriate range of OPDs between the interferometer arms 140 and 148. At a given OPD and flux-modulation frequency f, the phase and amplitude of the fluorescence signal (which may range, e.g., between kilohertz and several hundred megahertz) may be determined by mixing output of the detector 164 with a signal slightly shifted in modulation frequency by a frequency shift $\Delta f$, e.g., between a few hertz and a few hundred hertz, relative to the modulation frequency of the light source 112. The resulting signal has a component modulated at the relatively low cross-correlation frequency Δf, containing phase and amplitude information of the original fluorescent signal. The low-frequency component of the signal can be digitized and processed to extract the phase, amplitude and average flux density of the original relatively high-frequency fluorescent signal.

It should be noted that if an excitation source is flux-modulated at some fundamental frequency such that it contains harmonic content thereof (e.g., the excitation source is a laser pulsed at some fixed frequency, such as a mode-locked laser), a parallel data acquisition scheme could be employed to acquire frequency-domain data (e.g., phase, amplitude, average intensity) at the fundamental flux-modulation frequency and at a plurality of the harmonics of the fundamental flux-modulation frequency simultaneously. In such a scheme, the parallel acquisition of data at multiple harmonics would take place at a given OPD, and could be repeated at a series of different OPD values.

Figure 3:
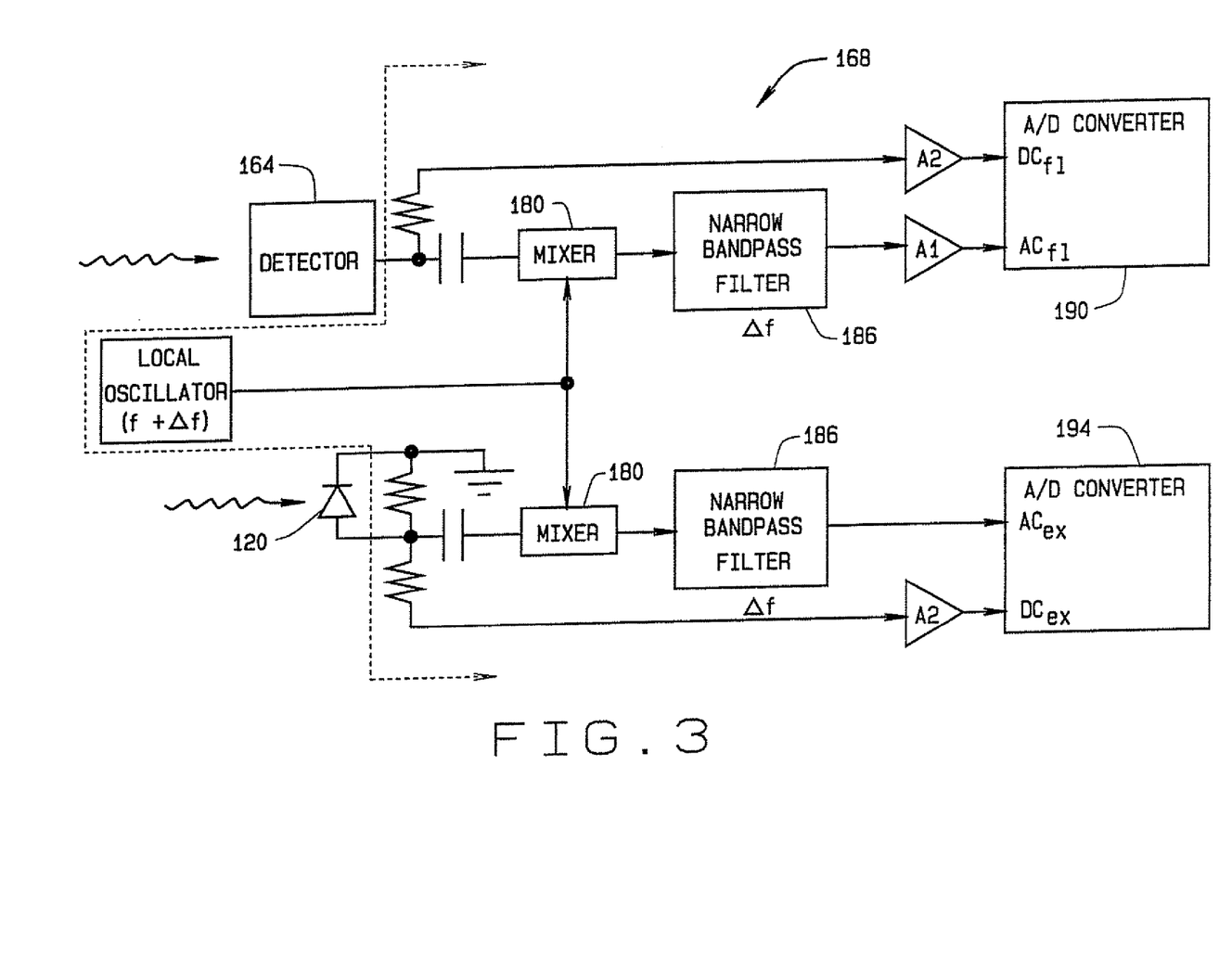
FIG. 3 is a schematic diagram of a heterodyning detection system of an apparatus for characterizing a fluorescent and/or phosphorescent material in accordance with one configuration of the present invention.

The heterodyning detection system 168 is shown in greater detail in FIG. 3. It should be noted that the detection system 168 is exemplary only, and that various configurations for heterodyning and extraction of phase, demodulation, amplitude, and average flux density from the detected signals could be used. The detection system 168 or some multi-stage heterodyning variant thereof would be appropriate for photodiode or microchannel plate detectors. If a photomultiplier tube detector were employed, the heterodyning means employed would typically involve modulation of the gain of the photomultiplier tube, as opposed to the mixing means external to the detectors that is employed in detection system 168. Signals emitted from the detector 164 and reference detector 120 are each separated into AC and DC components. The AC components are passed to mixers 180. The mixers 180 each also receive an input signal of frequency f+Δf from the local oscillator 172, f representing the flux modulation frequency generated by the master oscillator 108, and Δf representing the cross-correlation frequency. The signal of frequency f+Δf from the local oscillator 172 is coherent with the signal of frequency f generated by the master oscillator 108 of FIG. 2. Narrow bandpass filters 186 receive the mixed signals and pass the components of cross-correlation frequency Δf. An amplifier A1 amplifies AC signal and amplifiers A2 amplify DC signals. Referring to FIGS. 1 and 3, an A/D converter 190 converts the AC component $AC_{fl}$, and DC component $DC_{fl}$, to digital form, and an A/D converter 194 converts the AC component $AC_{ex}$ and DC component $DC_{ex}$ to digital form. The digital signals may be processed, for example, in the block 176 (shown in FIG. 2).

Output of the apparatus 100, after appropriate calibration, includes phase, demodulation, amplitude, and average fluorescence flux density data which may be plotted versus two axes, one axis representing OPD between the interferometer arms 140 and 148 and the other axis representing flux modulation frequency of the exciting light source 112 (kHz to MHz frequency scale). Output of the apparatus 100 effectively includes (after Fourier transformation of fluorescence data along both the flux-modulation frequency axis and the OPD axis) the spectrally resolved impulse response of a fluorescent sample to a Dirac delta-function excitation over an appropriately broad portion of the optical emission spectrum of the sample. The largest attainable OPD determines the spectral resolution of the apparatus, and the largest detectable flux-modulation frequency determines the temporal resolution of the apparatus.

Interferometer

The interferometer 128 in the present configuration is a step-scan instrument, which can be particularly appropriate for frequency-domain cross-correlation phase and amplitude measurements in accordance with various configurations. Step-scan interferometers are commercially available, for example, from Bruker Optics, Inc. of Billerica, Mass. In the interferometer 128, the moving mirror 152 that controls an OPD between the arms 140 and 148 moves incrementally on command. A step length and total number of steps to be taken during a scan are programmable. The beam splitter 136 is selected appropriately for a wavelength region of interest. The step-scan interferometer 128 permits heterodyne measurement to be performed during a mirror stationary state. Measured parameters include phase lag Φ, amplitudes AC and intensities DC as previously discussed with reference to FIGS. 1 and 3. Thus spectral and/or temporal artifacts that might occur, e.g., while using a continuous-scan interferometer can be avoided.

An interferogram resulting from a steady-state (time-invariant flux) light source impinging on an entrance aperture of an amplitude-splitting interferometer, e.g., the interferometer 128, can be described by $$I(z) = (1/2) \int_0^\infty R(\sigma)(1 + \cos(2\pi\sigma z))d\sigma \quad (1)$$

I(z) represents irradiance or flux density (power per unit area) at the detector resulting from the two-beam interference within the interferometer, and z represents the OPD between the arms 140 and 148 of the interferometer. R(σ) represents spectral power per unit area per wavenumber incident on the interferometer optics, where σ≡1/λ represents wavenumber (with units of inverse distance), and λ represents electromagnetic wavelength. Per equation 1, I(z) is related to R(σ) by a Fourier cosine transform.

Generally, the excitation light of a frequency-domain phase and modulation fluorometer can be described by $$E(t) = E_0[1 + M_{ex}\sin(2\pi ft)] \quad (2)$$

where t represents time, f represents frequency of the light flux modulation, and $M_{ex}$ represents modulation of the light source. The resultant fluorescence emitted by molecules illuminated by the flux described by equation (2) is given by $$F(t) = F_0[1 + M_{fl}\sin(2\pi ft + \phi)] \quad (3)$$

where F(t) represents fluorescence at a specific wavelength λ. The phase delay, φ, and the demodulation, $M = M_{fl}/M_{ex}$, arise from the finite lifetime of the excited state. φ and M can be defined in terms of the time-domain impulse response, I(t), of a fluorescent system to Dirac delta-function excitation:

$$\tan(\phi) = \frac{S}{G} \quad (4)$$

$$M = \frac{\sqrt{S^2 + G^2}}{N} \quad (5)$$

$$S(f) = \int_0^\infty I(t)\sin(2\pi ft)dt \quad (6)$$

$$G(f) = \int_0^\infty I(t)\cos(2\pi ft)dt \quad (7)$$

$$N = \int_0^\infty I(t)dt \quad (8)$$

Figure 1:
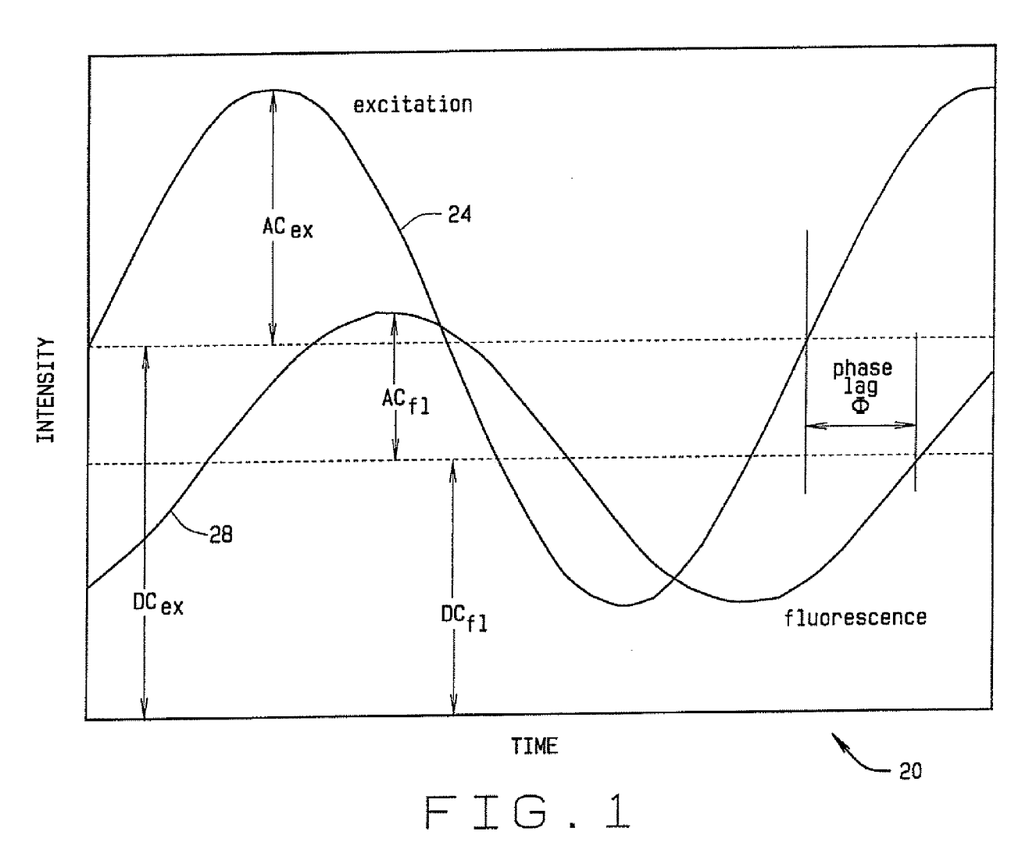
FIG. 1 is a graph representing time evolution of light source intensity and a resultant emission from a fluorescent sample in accordance with one implementation of the present invention.

-continued $$DC_{fl} = F_0 = E_0 N \quad (9)$$

$$M_{fl} = M_{ex}\frac{\sqrt{S^2 + G^2}}{N} \quad (10)$$

$$AC_{fl} = E_0 M_{ex}\sqrt{S^2 + G^2} \quad (11)$$

where measured parameters $\Phi$, AC, and DC are as described, for example, with reference to FIG. 1, $M \equiv M_{fl}/M_{ex}$ with $M_{fl} \equiv AC_{fl}/DC_{fl}$, and $M_{ex} \equiv AC_{ex}/DC_{ex}$.

If the fluorescence decay is mono-exponential, that is, the impulse response of the system is $$I(t) = I_0 e^{\frac{-t}{\tau}}, \quad (12)$$

where $\tau$ is a constant representing the characteristic decay time (i.e., the fluorescence lifetime) of the emission, then $$S(f) = \frac{I_0 2\pi f \tau^2}{1 + (2\pi f)^2 \tau^2} \quad (13)$$

$$G(f) = \frac{I_0 \tau}{1 + (2\pi f)^2 \tau^2} \quad (14)$$

$$N = I_0 \tau \quad (15)$$

$$\tan(\phi) = 2\pi f \tau \quad (16)$$

$$M(f) = \frac{M_{fl}}{M_{ex}} = \frac{1}{\sqrt{1 + (2\pi f)^2 \tau^2}} \quad (17)$$

$$AC_{fl} = E_o M_{ex}\frac{I_o \tau}{\sqrt{1 + (2\pi f)^2 \tau^2}} \quad (18)$$

$$DC_{fl} = E_o N \quad (19)$$

Consider the time-domain impulse response $R(\sigma,t)$ of a fluorescent system to Dirac delta-function excitation, where $\sigma$ represents the wavenumber of the fluorescence. If the impulse response $R(\sigma,t)$ passes through an amplitude splitting interferometer, the resultant light flux exiting the interferometer is given by $$I(z, t) = \frac{1}{2}\int_0^\infty R(\sigma, t)(1 + \cos(2\pi\sigma z))d\sigma \quad (20)$$

where z represents the interferometer OPD. If the exciting light were instead given by equation (2), then equations (6) through (8) would now be expressed as follows:

$$S(z, f) = \int_0^\infty I(z, t)\sin(2\pi f t)dt \quad (21)$$

$$G(z, f) = \int_0^\infty I(z, t)\cos(2\pi f t)dt \quad (22)$$

$$N(z) = \int_0^\infty I(z, t)dt \quad (23)$$

The relationships given in equations (4), (5), (9), (10), and (11) remain the same, but with $\Phi$, M, and AC now functions of optical path difference z and excitation modulation frequency f, that is, $\Phi(z,f)$, $M(z,f)$, and $AC(z,f)$.

EXAMPLE 1

Box Function Spectrum, Mono-Exponential Decay With Lifetime $\tau$ At All Wavelengths Consider a fluorescent system with the following impulse response:

$$R(\sigma, t) = \begin{cases} I_o e^{-t/\tau} & \sigma_1 \leq \sigma \leq \sigma_2 \\ 0 & \text{otherwise} \end{cases} \quad (24)$$

Inserting equation (24) into equation (20) gives $$I(z, t) = \frac{I_o e^{-t/\tau}}{2}\int_{\sigma_1}^{\sigma_2}(1 + \cos(2\pi\sigma z))d\sigma, \quad (25)$$

which yields the time-domain response $$I(z, t) = \frac{I_o}{2}(\sigma_2 - \sigma_1)\left[\left(1 + \cos[\pi z(\sigma_1 + \sigma_2)]\frac{\sin[\pi z(\sigma_2 - \sigma_1)]}{\pi z(\sigma_2 - \sigma_1)}\right)\right]e^{-t/\tau} \quad (26)$$

Insertion of equation (26) into equations (21), (22), and (23) respectively gives the frequency-domain response, $$S(z, f) = \frac{I_o}{2}(\sigma_2 - \sigma_1)\left[\left(1 + \cos[\pi z(\sigma_1 + \sigma_2)]\frac{\sin[\pi z(\sigma_2 - \sigma_1)]}{\pi z(\sigma_2 - \sigma_1)}\right)\right] \quad (27)$$

$$\left[\frac{2\pi f \tau^2}{1 + (2\pi f)^2 \tau^2}\right]$$

$$G(z, f) = \frac{I_o}{2}(\sigma_2 - \sigma_1)\left[\left(1 + \cos[\pi z(\sigma_1 + \sigma_2)]\frac{\sin[\pi z(\sigma_2 - \sigma_1)]}{\pi z(\sigma_2 - \sigma_1)}\right)\right] \quad (28)$$

$$\left[\frac{\tau}{1 + (2\pi f)^2 \tau^2}\right]$$

$$N(z) = \frac{I_o}{2}(\sigma_2 - \sigma_1)\left[\left(1 + \cos[\pi z(\sigma_1 + \sigma_2)]\frac{\sin[\pi z(\sigma_2 - \sigma_1)]}{\pi z(\sigma_2 - \sigma_1)}\right)\right]\tau \quad (29)$$

Note that inserting equations (27), (28), and (29) into equations (4) and (5) yields expressions for $\phi(z,f)$ and $M(z,f)$ that are the same as equations (16) and (17) respectively, i.e., $$\tan(\phi(z, f)) = 2\pi f \tau \quad (30)$$

and $$M(z, f) = \frac{1}{\sqrt{1 + (2\pi f)^2 \tau^2}} \quad (31)$$

Note that both $\phi$ and M are independent of the interferometer optical path difference z in this particular example. Note also that the result of equations (30) and (31) is true for any mono-exponentially decaying system in which the impulse response is given by $R(\sigma,t)=\tilde{R}(\sigma)e^{-t/\tau}$, where $\tilde{R}(\sigma)$ is an arbitrary steady-state emission spectrum. The result of equations (30) and (31) is not likely to be true in general if the impulse response of a fluorescent system is characterized by a plurality of fluorescence lifetimes.

Assuming an excitation described by equation (2), $AC_{fl}(z,f)$ is given via equation (11) as $$AC_{fl}(z, f) = \quad (32)$$

$$E_o M_{ex} \frac{I_o}{2}(\sigma_2 - \sigma_1)\left[\left(1 + \cos[\pi z(\sigma_1 + \sigma_2)]\frac{\sin[\pi z(\sigma_2 - \sigma_1)]}{\pi z(\sigma_2 - \sigma_1)}\right)\right]$$

$$\frac{\tau}{\sqrt{1 + (2\pi f)^2 \tau^2}}$$

EXAMPLE 2

Two Overlapping Box-Function Spectra, Each With Different Mono-Exponential Decay Rates $\tau_1$ and $\tau_2$ $$R(\sigma, t) = \begin{cases} I_o e^{-t/\tau_1} & \sigma_1 \le \sigma \le \sigma_2 \\ I_o(e^{-t/\tau_1} + e^{-t/\tau_2}) & \sigma_2 < \sigma \le \sigma_3 \\ I_o e^{-t/\tau_2} & \sigma_3 < \sigma \le \sigma_4 \\ 0 & \text{otherwise} \end{cases} \quad (33)$$

Inserting equation (33) into equation (20) gives $$I(z, t) = \frac{I_o e^{-t/\tau_1}}{2}\int_{\sigma_1}^{\sigma_2}(1 + \cos(2\pi\sigma z))d\sigma + \quad (34)$$

$$\frac{I_o(e^{-t/\tau_1} + e^{-t/\tau_2})}{2}\int_{\sigma_2}^{\sigma_3}(1 + \cos(2\pi\sigma z))d\sigma +$$

$$\frac{I_o e^{-t/\tau_2}}{2}\int_{\sigma_3}^{\sigma_4}(1 + \cos(2\pi\sigma z))d\sigma$$

which yields the time-domain response $$I(z, t) = \quad (35)$$

$$\frac{I_o}{2}(\sigma_2 - \sigma_1)\left[\left(1 + \cos[\pi z(\sigma_1 + \sigma_2)]\frac{\sin[\pi z(\sigma_2 - \sigma_1)]}{\pi z(\sigma_2 - \sigma_1)}\right)\right]e^{-t/\tau_1} +$$

$$\frac{I_o}{2}(\sigma_3 - \sigma_2)\left[\left(1 + \cos[\pi z(\sigma_2 + \sigma_3)]\frac{\sin[\pi z(\sigma_3 - \sigma_2)]}{\pi z(\sigma_3 - \sigma_2)}\right)\right]$$

$$(e^{-t/\tau_1} + e^{-t/\tau_2}) +$$

$$\frac{I_o}{2}(\sigma_4 - \sigma_3)\left[\left(1 + \cos[\pi z(\sigma_3 + \sigma_4)]\frac{\sin[\pi z(\sigma_4 - \sigma_3)]}{\pi z(\sigma_4 - \sigma_3)}\right)\right]e^{-t/\tau_2}$$

Insertion of equation (35) into equations (21), (22), and (23) respectively gives the frequency-domain response, $$S(z, f) = \frac{I_o}{2}(\sigma_2 - \sigma_1)\left[\left(1 + \cos[\pi z(\sigma_1 + \sigma_2)]\frac{\sin[\pi z(\sigma_2 - \sigma_1)]}{\pi z(\sigma_2 - \sigma_1)}\right)\right]\left[\frac{2\pi f \tau_1^2}{1 + (2\pi f)^2 \tau_1^2}\right] + \quad (36)$$

$$\frac{I_o}{2}(\sigma_3 - \sigma_2)\left[\left(1 + \cos[\pi z(\sigma_2 + \sigma_3)]\frac{\sin[\pi z(\sigma_3 - \sigma_2)]}{\pi z(\sigma_3 - \sigma_2)}\right)\right]$$

$$\left[\frac{2\pi f \tau_1^2}{1 + (2\pi f)^2 \tau_1^2} + \frac{2\pi f \tau_2^2}{1 + (2\pi f)^2 \tau_2^2}\right] +$$

$$\frac{I_o}{2}(\sigma_4 - \sigma_3)\left[\left(1 + \cos[\pi z(\sigma_3 + \sigma_4)]\frac{\sin[\pi z(\sigma_4 - \sigma_3)]}{\pi z(\sigma_4 - \sigma_3)}\right)\right]\left[\frac{2\pi f \tau_2^2}{1 + (2\pi f)^2 \tau_2^2}\right]$$

$$G(z, f) = \frac{I_o}{2}(\sigma_2 - \sigma_1)\left[\left(1 + \cos[\pi z(\sigma_1 + \sigma_2)]\frac{\sin[\pi z(\sigma_2 - \sigma_1)]}{\pi z(\sigma_2 - \sigma_1)}\right)\right]\left[\frac{\tau_1}{1 + (2\pi f)^2 \tau_1^2}\right] + \quad (37)$$

$$\frac{I_o}{2}(\sigma_3 - \sigma_2)\left[\left(1 + \cos[\pi z(\sigma_2 + \sigma_3)]\frac{\sin[\pi z(\sigma_3 - \sigma_2)]}{\pi z(\sigma_3 - \sigma_2)}\right)\right]$$

$$\left[\frac{\tau_1}{1 + (2\pi f)^2 \tau_1^2} + \frac{\tau_2}{1 + (2\pi f)^2 \tau_2^2}\right] +$$

$$\frac{I_o}{2}(\sigma_4 - \sigma_3)\left[\left(1 + \cos[\pi z(\sigma_3 + \sigma_4)]\frac{\sin[\pi z(\sigma_4 - \sigma_3)]}{\pi z(\sigma_4 - \sigma_3)}\right)\right]\left[\frac{\tau_2}{1 + (2\pi f)^2 \tau_2^2}\right]$$

$$N(z) = \frac{I_o}{2}(\sigma_2 - \sigma_1)\left[\left(1 + \cos[\pi z(\sigma_1 + \sigma_2)]\frac{\sin[\pi z(\sigma_2 - \sigma_1)]}{\pi z(\sigma_2 - \sigma_1)}\right)\right]\tau_1 + \quad (38)$$

$$\frac{I_o}{2}(\sigma_3 - \sigma_2)\left[\left(1 + \cos[\pi z(\sigma_2 + \sigma_3)]\frac{\sin[\pi z(\sigma_3 - \sigma_2)]}{\pi z(\sigma_3 - \sigma_2)}\right)\right](\tau_1 + \tau_2) +$$

$$\frac{I_o}{2}(\sigma_4 - \sigma_3)\left[\left(1 + \cos[\pi z(\sigma_3 + \sigma_4)]\frac{\sin[\pi z(\sigma_4 - \sigma_3)]}{\pi z(\sigma_4 - \sigma_3)}\right)\right]\tau_2$$

Note that the expressions yielded for $\phi(z,f)$ and $M(z,f)$ by inserting equations (36), (37) and (38) into equations (4) and (5) respectively are fairly complex expressions in z and f, as compared with the relatively simple expressions obtained for the mono-exponentially decaying box-function spectrum of Example 1.

Measurement and Calibration

Assume that a fluorescent sample is excited by a flux modulated light source described by the following equation (39), and the resultant fluorescence of the sample is described by the following equation (40):

$$E(t) = E_0[1 + M_{ex}\sin(2\pi ft)](\text{excitation signal}) \quad (39)$$

$$F(z,t) = F_o(z)[1 + M_{fl}(z,f)\sin(2\pi ft + \phi(z,f))](\text{fluorescence signal}) \quad (40)$$

where z represents the optical path difference generated by the interferometer and f represents the flux modulation frequency. The fluorescence signal is mixed with a cross-correlation signal that has a coherent phase relationship with respect to the excitation signal (i.e., the signals are phase-locked). The cross-correlation signal, generated by a local oscillator such as shown in FIG. 3, is given by $$C(t) = C_o[1 + M_c\sin(2\pi(f + \Delta f)t + \beta)] \quad (41)$$

The signal P(z,t) that results from the mixing is the product of the two signals, that is, $P(z, t) = F(z, t) \cdot C(t)$, yielding $$P(z, t) = F_o(z) \quad (42)$$
$$C_o[1 + M_{fl}(z, f)\sin(2\pi ft + \phi(z, f)) + M_c\sin(2\pi(f + \Delta f)t + \beta) +$$
$$M_{fl}(z, f)M_c\sin(2\pi ft + \phi(z, f))\sin(2\pi(f + \Delta f)t + \beta)]$$

The last term of equation (42) can be written as $$\frac{M_{fl}(z, f)M_c}{2}\begin{bmatrix} \cos(2\pi\Delta ft + \Delta\phi(z, f)) - \\ \cos(4\pi ft + 2\pi\Delta ft + (\beta + \phi(z, f))) \end{bmatrix} \quad (43)$$

where $\Delta\phi(z,f) \equiv \beta(f) - \phi(z,f)$. After low-pass or other appropriate filtering, only the DC and low-frequency AC term (i.e., the $\Delta f$ term) remain, and $P(z,t)$ thus becomes $$P(z, t) = F_o(z)C_o\left[1 + \frac{M_{fl}(z, f)M_c}{2}\cos(2\pi\Delta ft + \Delta\phi(z, f))\right] \quad (44)$$

The high frequency information contained in equation (40), (which may be of the order of tens to hundreds of Megahertz in a frequency-domain fluorescence measurement), is thereby mapped into a lower-frequency signal which is more readily digitized by an analog-to-digital converter than the original high-frequency signal. Thus a fluorescence signal emitted at flux modulation frequency of f is mapped into a signal of much lower frequency $\Delta f$ that retains essentially all of the information contained in the original high-frequency signal.

Calibration

Calibration is performed to compensate for electronic phase shifts and modulation introduced by the detector and electronics. System (optical) spectral characteristics may be determined using known methods. A reference material of known fluorescence lifetime (lifetime=$\tau_{ref}$, i.e., mono-exponential temporal decay across the instrument spectral band) may be utilized for calibration. Values for phase shift and demodulation may be calculated using the known lifetime $\tau_{ref}$ in equations (30) and (31) respectively. Phase shift $\Delta\phi_{ref}$ and demodulation $M_{ref}$ of the reference material may be measured at a given optical path difference z and flux modulation frequency f (per equations (30) and (31). Phase shift $\phi$ and demodulation M are independent of z for a mono-exponentially decaying system. The measured values $\Delta\phi_{ref}(f)$ and $M_{ref}(f)$ are compared to the values calculated using the known lifetime $\tau_{ref}$, yielding, from equation (44), $$\beta(f) = \Delta\phi_{ref}(f) + \tan^{-1}(2\pi f \tau_{ref}) \quad (45)$$

$$M_c(f) = \frac{2M_{ref}}{M_{fl}} = 2M_{ref}(f)\sqrt{1 + (2\pi f)^2 \tau_{ref}^2} \quad (46)$$

An unknown sample also may be measured, yielding uncalibrated sample phase and demodulation values respectively given by $\Delta\phi_{samp}(z,f)$ and $M_{samp}(z,f)$. Recalling that $\Delta\phi(z,f) \equiv \beta(f) - \phi(z,f)$, calibrated sample phase and demodulation values are respectively given by $$\phi_{cal}(z, f) = \Delta\phi_{ref}(f) - \Delta\phi_{samp}(z, f) + \tan^{-1}(2\pi f \tau_{ref}) \quad (47)$$

$$M_{cal}(z, f) = \frac{M_{samp}(z, f)}{M_{ref}(f)\sqrt{1 + (2\pi f)^2 \tau_{ref}^2}}. \quad (48)$$

Measurements may alternate between the unknown sample and the known reference material until the uncertainty in $\phi_{cal}(z,f)$ and $M_{cal}(z,f)$ has been reduced to an acceptable level.

Examples included in this description are for illustrative purposes only and are not to be construed as limiting the scope of the invention.

As indicated above, calibration materials preferably exhibit mono-exponential fluorescent decay. Potential calibration materials include lanthanide and transition metal cations doped into crystalline and glass hosts, and/or organic fluorescent dyes. Lanthanide- and transition metal-doped materials are available in wide variety, as are organic fluorescent materials. Excitation bands usually exist in the UV and violet spectral regions, and fluorescence bands exist from the UV to IR, depending on the material. An extensive decay time data base exists in the literature for those materials used in lasers.

The foregoing configurations and methods provide a measurement system that has higher optical throughput than conventional methods. Thus both a temporal response (e.g., impulse response) and spectral response of a fluorescent or phosphorescent system can be determined rapidly, at impulse-response time scales ranging from sub-picoseconds to milliseconds, and at wavelengths spanning the near ultraviolet, visible, and infrared portion of the electromagnetic spectrum. High resolution is provided along both spectral and temporal axes of a fluorescence (and/or phosphorescence) flux data set. Because it is possible to use a single detector to detect the fluorescence and/or phosphorescence, calibration and electronic circuitry can be greatly simplified compared to prior art time-resolved dispersive/detector array systems. Such prior art systems may also suffer from relatively slow temporal response compared to a single-detector system in accordance with configurations of the present invention. Configurations of the present invention make it possible to circumvent throughput problems (e.g., signal-to-noise problems) encountered using prior-art monochromator-based single-detector frequency domain fluorometer systems and/or dispersive/detector array frequency domain fluorometer systems. At the same time, configurations of the present invention can provide spectral measurements comparable or superior in breadth and resolution to those provided by scanning monochromator-based frequency domain fluorometer systems and/or dispersive/detector array based frequency domain fluorometer systems.

High optical throughput of the invention, coupled with near parallel acquisition of high resolution temporal and spectral data, allows for rapid characterization of trace materials, as well as the assessment of the molecular dynamics of these materials. This is of great interest in biochemistry, medicine, homeland security, environmental science, and other related fields.

While various preferred embodiments have been described, those skilled in the art will recognize modifications or variations which might be made without departing from the inventive concept. The examples illustrate the invention and are not intended to limit it. Therefore, the description and claims should be interpreted liberally with only such limitation as is necessary in view of the pertinent prior art.

What is claimed is:

1. A method of characterizing fluorescence and/or phosphorescence of a material comprising the steps of:
    using an excitation signal to excite the material;
    introducing an optical path difference between portions of an emission signal produced by the excited material to obtain an interference signal;
    using the interference signal and a cross-correlation frequency of the interference and excitation signals to resolve the emission signal to determine a response of the material to excitation.

2. The method of claim 1, further comprising using the optical path difference and a frequency of the emission signal to determine at least one of the following: a phase difference between the excitation and emission signals, a demodulation, and an emission signal amplitude.

3. The method of claim 1, wherein introducing an optical path difference comprises using an interferometer.

4. The method of claim 1, further comprising detecting the interference signal at a single detector.

5. The method of claim 1, further comprising detecting the interference signal at an array of detectors.

6. The method of claim 1, further comprising performing said steps for each of a plurality of flux modulation frequencies of the excitation signal.

7. The method of claim 6, performed for each of a plurality of optical path differences.

8. The method of claim 1, further comprising comparing the interference signal with a reference signal to determine a phase of the emission signal.

9. The method of claim 1, wherein the emission signal is resolved spectrally and temporally.

10. An apparatus for characterizing fluorescent and/or phosphorescent material, the apparatus comprising:
    an excitation source that provides an excitation signal for exciting the material;
    an interferometer and a single detector, the interferometer configured to receive an emission signal from the excited material and provide an optical path difference between portions of the received emission signal to produce an interference signal at the detector; and
    a heterodyning detection system configured to mix a cross-correlation signal of the excitation signal with the detected interference signal to resolve the emission signal.

11. The apparatus of claim 10, wherein the excitation source provides a plurality of flux-modulated excitation signals relative to the optical path difference, the apparatus further configured to use the plurality of excitation signals and the optical path difference to resolve the emission signal.

12. The apparatus of claim 10, wherein the intederometer comprises a step-scan interferometer.

13. The apparatus of claim 10, wherein the interferometer comprises a collimator that collimates the emission signal, and a condenser that condenses the interference signal.

14. The apparatus of claim 10, wherein the heterodyning detection system comprises a local oscillator configured to provide the cross-correlation signal.

15. The apparatus of claim 10, further configured to use the optical path difference and a frequency of the emission signal to determine at least one of the following: a phase difference between the excitation and emission signals, a demodulation, and an emission signal amplitude.

16. An apparatus for spectrally and temporally characterizing fluorescent and/or phosphorescent material comprising:
    means for producing an excitation frequency to excite the material;
    means for collecting an emission signal from the excited material;
    means for providing an optical path difference between portions of the collected signal to produce a signal representative of interference between the portions;
    means for detecting the signal representative of interference;
    means for mixing a cross-correlation frequency of the excitation frequency with the detected signal to obtain a mixed signal; and
    means for using the mixed signal to resolve the emission signal.

17. The apparatus of claim 16, further comprising means for using the optical path difference and a frequency of the emission signal to determine at least one of the following: a phase difference between the excitation frequency and emission signal, a demodulation, and an emission signal amplitude.

18. The apparatus of claim 16, wherein the detecting means comprises a single detector.

19. The apparatus of claim 16, further comprising means for producing the cross-correlation frequency.

20. The apparatus of claim 16, configured to temporally and spectrally resolve the emission signal.

* * * * *